(12) United States Patent
Lecomte et al.

(10) Patent No.: US 6,969,408 B2
(45) Date of Patent: Nov. 29, 2005

(54) LOW PROFILE ACTIVE SHOCK MODULE PROSTHESIS

(75) Inventors: Christophe Guy Lecomte, Reykjavik (IS); Heidrun Gigja Ragnarsdottir, Reykjavik (IS)

(73) Assignee: Ossur Engineering, Inc., Albion, MI (US)

( * ) Notice: Subject to any disclaimer, the term of this patent is extended or adjusted under 35 U.S.C. 154(b) by 0 days.

(21) Appl. No.: 10/674,736

(22) Filed: Sep. 30, 2003

(65) Prior Publication Data

US 2005/0071017 A1    Mar. 31, 2005

(51) Int. Cl.$^7$ ................................. A61F 2/24
(52) U.S. Cl. ...................................... 623/55
(58) Field of Search ..................... 623/55, 53, 52, 623/50, 47–49

(56) References Cited

U.S. PATENT DOCUMENTS

| | | |
|---|---|---|
| 53,931 A | 4/1866 | Weston et al. |
| 277,562 A | 5/1883 | Furrer |
| 809,875 A | 1/1906 | Wilkins |
| 817,340 A | 4/1906 | Rosenkranz |
| 827,720 A | 8/1906 | Erwin |
| 1,779,765 A | 10/1930 | Eichhorn |
| 1,996,874 A | 4/1935 | Mascau |
| 2,443,356 A | 6/1948 | Mathis |
| 2,480,856 A | 9/1949 | Henschke et al. |
| 2,570,735 A | 10/1951 | Weise |
| 2,578,019 A | 12/1951 | Ryan |
| 2,617,115 A | 11/1952 | Ellery |
| 2,619,652 A | 12/1952 | Vesper |
| 2,692,392 A | 10/1954 | Bennington et al. |
| 2,699,554 A | 1/1955 | Comelli |
| 2,843,853 A | 7/1958 | Mauch |
| 2,899,685 A | 8/1959 | Bourcier de Carbon |
| 3,663,967 A | 5/1972 | Vermillion |
| 3,707,731 A | 1/1973 | Morgan |
| 3,800,333 A | 4/1974 | Friberg |
| 3,800,334 A | 4/1974 | Friberg |
| 3,906,552 A | 9/1975 | Weber |
| 3,956,775 A | 5/1976 | Moore |
| 4,038,705 A | 8/1977 | Owens |
| 4,161,042 A | 7/1979 | Cottingham et al. |
| 4,216,550 A | 8/1980 | Thompson |
| 4,370,761 A | 2/1983 | Serri |
| 4,461,045 A | 7/1984 | Shorter et al. |
| 4,463,459 A | 8/1984 | Shorter et al. |
| 4,555,817 A | 12/1985 | McKendrick |
| 4,605,417 A | 8/1986 | Fleischauer |

(Continued)

FOREIGN PATENT DOCUMENTS

DE    328017    2/1919

(Continued)

OTHER PUBLICATIONS

Article entitled "Titanium Elastic Properties and Applicaitons from Springs," Oct. 1987.

(Continued)

*Primary Examiner*—Alvin J. Stewart
(74) *Attorney, Agent, or Firm*—Knobbe Martens Olson & Bear, LLP

(57) ABSTRACT

In one embodiment, an impact and torque-absorbing module for a low profile lower limb prosthesis comprises two support members telescopingly engaged to permit axial and rotational motion therebetween. A resilient element resists axial displacement of the two support members, and a torque resisting cuff resists rotational displacement of the two support members. Precompression of the resilient element can reduce the size of the shock module making it more compact. The resilient element can also be replaced allowing adjustment of the shock absorption.

12 Claims, 5 Drawing Sheets

U.S. PATENT DOCUMENTS

| | | | |
|---|---|---|---|
| 4,619,660 A | 10/1986 | Christiansen et al. | |
| 4,728,336 A | 3/1988 | Cooper | |
| 4,865,611 A | 9/1989 | Al-Turaiki | |
| 4,883,493 A | 11/1989 | Martel et al. | |
| 4,938,775 A | 7/1990 | Morgan | |
| 4,994,086 A | 2/1991 | Edwards | |
| 5,019,109 A | 5/1991 | Voisin | |
| 5,030,239 A | 7/1991 | Copes | |
| 5,071,435 A | 12/1991 | Fuchs et al. | |
| 5,112,356 A | 5/1992 | Harris et al. | |
| 5,116,383 A | 5/1992 | Shorter et al. | |
| 5,376,133 A | 12/1994 | Gramnas | |
| 5,376,138 A | 12/1994 | Bouchard et al. | |
| 5,405,411 A | 4/1995 | McCoy | |
| 5,425,781 A | 6/1995 | Allard et al. | |
| 5,458,656 A * | 10/1995 | Phillips | 623/27 |
| 5,482,513 A | 1/1996 | Wilson | |
| 5,702,488 A | 12/1997 | Wood et al. | |
| 5,720,474 A | 2/1998 | Sugiyama | |
| 5,728,175 A | 3/1998 | Rincoe | |
| 5,769,896 A | 6/1998 | Rosendahl et al. | |
| 5,800,562 A * | 9/1998 | Wilkinson | 623/27 |
| 5,800,563 A | 9/1998 | Arbogast et al. | |
| 5,888,214 A | 3/1999 | Ochoa | |
| 5,904,721 A | 5/1999 | Henry et al. | |
| 5,961,556 A | 10/1999 | Thorn | |
| 5,984,972 A | 11/1999 | Huston et al. | |
| 6,080,197 A * | 6/2000 | Chen | 623/27 |
| 6,120,547 A * | 9/2000 | Christensen | 623/52 |
| 6,302,918 B1 * | 10/2001 | Gramnas | 623/27 |
| 6,468,315 B1 | 10/2002 | Wilkinson et al. | |
| 6,478,826 B1 | 11/2002 | Phillips et al. | |
| 6,511,512 B2 * | 1/2003 | Phillips et al. | 623/27 |
| 6,699,295 B2 * | 3/2004 | Lee et al. | 623/49 |
| 6,743,260 B2 * | 6/2004 | Townsend et al. | 623/52 |
| 6,764,521 B2 * | 7/2004 | Molino et al. | 623/52 |

FOREIGN PATENT DOCUMENTS

| | | |
|---|---|---|
| DE | 196 42 719 A1 | 4/1997 |
| EP | 0255556 A1 | 2/1988 |
| EP | 0 738 837 A2 | 10/1996 |
| EP | 0 606 383 B1 | 3/1997 |
| FI | 941453 | 5/1994 |
| FR | 2501999 | 9/1982 |
| FR | 2567395 | 1/1986 |
| GB | 1550658 | 8/1979 |
| GB | 2 305 363 A | 8/1996 |
| JP | 8-280870 | 10/1996 |
| JP | 8-284995 | 11/1996 |
| SU | 605613 | 5/1978 |
| WO | WO 93/06795 | 4/1993 |
| WO | WO 00/27317 | 5/2000 |

OTHER PUBLICATIONS

Article entitled "Titanium Alloy Springs from Springs," May 1988.

Brochure entitled "MaxLife Die Springs," Dayton Progress Corporation.

International Search Report, PCT/US2004/031515, Filing date: Sep. 27, 2004.

Written opinion of the international searching authority, PCT/US2004/031515, Filing date: Sep. 27, 2004.

* cited by examiner

LOW PROFILE ACTIVE SHOCK MODULE PROSTHESIS

BACKGROUND OF THE INVENTION

1. Field of the Invention

Embodiments of the present invention relate to lower limb prostheses in general, and, in certain embodiments, to a low profile shock module prosthesis having a resilient element and a torque-resisting cuff permitting rotational compliance between the lower leg and foot.

2. Description of the Related Art

Various types of lower limb prostheses are known in the prior art. Such devices generally include some form of attachment for coupling the device to the dorsal end of the limb and for extending to the ground to provide body support. Moreover, these devices generally constitute attempts to simulate the structure and/or the performance of the human leg and foot.

The various prostheses known in the prior art include some prostheses designed for people who have long residual limbs. For these patients, the calf and shin functions as the stump for prosthetic purposes. Thus, any prosthetic device utilized by the patient must either be relatively compact so as to be attachable below the point of amputation, or must be configured to accommodate the patient's shin and calf while attached thereto or higher up on the wearer's leg.

Among the features desirable in a lower limb prosthesis is the incorporation of some means for providing impact absorption and/or dampening during use of the prosthesis, without sacrificing the ability to reliably and predictably support the amputee's body weight. Such impact absorption permits the amputee to participate in activities with comfort and minimal stump trauma, hence allowing the amputee to be mobile for longer periods of time. Also desirable is a convenient means to selectively adjust the degree of impact absorption to suit the particular attributes (e.g., weight) and activity (e.g., walking, running, jumping, etc.) of the amputee.

Another desirable feature of lower limb prostheses is the incorporation of some means for allowing rotational compliance of the lower leg and foot relative to the stump of the amputee. Such rotation is beneficial and simulates the action of a natural human knee/ankle in a number of activities that involve the twisting of a person's body with respect to their planted foot, such as golf, tennis, and the like. Unrestrained compliance, however, is undesirable, as the foot would be free to twist unnaturally. Thus, it is desirable to incorporate a means for providing torsion-resistance against the rotation of a lower leg and foot relative to the stump of the amputee, and for returning the foot to its natural forward orientation after each rotational movement.

Impact absorption in lower limb prostheses can be achieved through the use of two or more elongated telescoping members with a resilient means disposed therebetween. Axial forces acting on such members cause relative longitudinal motion between them with the resilient means providing energy storage and release. Due to the vertical height of some of the pylons, those shock-absorbing prostheses cannot accommodate the shin and calf of an amputee with a long residual limb.

Thus, although the prior art illustrates many impact absorbing prostheses, few, if any, are designed to be compact enough for use by patients with long residual limbs. Furthermore, none of the prior art sets forth a lower limb prosthesis for amputees with long residual limbs that can provide both impact absorption and rotational compliance with torsion-resistance.

SUMMARY OF THE INVENTION

In accordance with one embodiment, the present invention provides an impact and torque absorbing prosthetic shock module for a low profile prosthesis to accommodate amputees with long residual limbs. The shock module comprises an inner and an outer support member each having a hollow cylindrical, tube shaped portion. The two support members are coaxially aligned and telescopingly engaged with one another. A resilient element resists axial displacement of the support members providing shock absorption, and a torque-resisting cuff provides resists relative rotational motion between the support members providing torque absorption. In one embodiment, precompression of the resilient element can help to reduce the overall height of the shock module, as can a bearing that improves the fit between the support members. In addition, in some embodiments of the invention, the lower support member extends into the space surrounded by the torque resisting cuff. Also, in some embodiments, the torque-resisting cuff has a reduced horizontal cross section that can aid in fitting the shock module within a cosmetic ankle or cosmetic foot cover.

In another embodiment of the invention, the resilient element can be removed allowing the prosthetist or amputee to replace the resilient element. Different resilient elements can provide different degrees of shock absorption. The resilient element can be removed through removal of the fitting that attaches the prosthesis to a socket or an intermediate prosthetic device.

In some embodiments of the invention, the shock module has a height of no more than about 150 mm, more preferably no more than about 130 mm, and even more preferably no more than about 120 mm. Also, in some embodiments of the invention, the lower support member has a base with an inclined attachment section designed to correspond with an inclined attachment section on a prosthetic foot. That type of attachment can allow for a lower profile since the inclined portion of the prosthetic foot can continue to slope upward behind the shock module.

In one embodiment, the shock module comprises inner and outer support members which are coaxially supported relative to one another and capable of relative rotation and axial translation. The shock module also comprises a resilient element that resists axial displacement of the support members, and a torque resisting cuff. The torque-resisting cuff provides torsional resistance to relative rotational motion between the support members and has a generally tubular shape. The cuff is proximally attached to an outer surface of one of the support members and is distally attached to an outer surface of the other support member. The shock module further comprises an adapter for proximally attaching the shock module to a stump supporting socket or intermediate device. The adapter can be at least partly removed to allow replacement of the resilient element.

In another embodiment, the shock module comprises inner and outer support members which are coaxially supported relative to one another and capable of relative rotation and axial translation. The shock module further comprises a precompressed resilient element that resists axial displacement of the support members. A generally tubular shaped torque resisting cuff provides torsional resistance to relative rotational motion between the support members.

The cuff is proximally attached to an outer surface of one of the support members and is distally attached to an outer surface of the other support member. The shock module also comprises an adapter for proximally attaching the shock module to a stump-supporting socket or intermediate device.

In yet another embodiment, an impact and torque absorbing lower limb prosthesis comprises upper and lower support members that are coaxially supported relative to one another and capable of relative rotation and axial translation. The prosthesis further comprises a resilient element that resists axial displacement of the support members. The prosthesis also comprises a torque resisting cuff with a generally tubular shape. The torque resisting cuff provides torsional resistance to relative rotational motion between the support members, and it is proximally attached to an outer surface of one of the support members and distally attached to an outer surface of the other support member. In addition, the prosthesis comprises an adapter operably connected to the upper support member for proximally attaching the shock module to a stump-supporting socket or intermediate device. Operably connected to the lower support member is a prosthetic foot member that has a ground contacting portion adapted to contact a ground surface. The vertical height from the ground contacting portion of the foot to the top of the adapter in one embodiment is about 150 mm or less.

In another embodiment, a shock module comprises upper and lower support members that are coaxially supported relative to one another and are capable of relative rotation and axial translation. The shock module further comprises a torque resisting cuff that provides torsional resistance to relative rotational motion between the support members. The torque resisting cuff, which has a generally tubular shape, is proximally attached to an outer surface of one of the support members and distally attached to an outer surface of the other support member. The shock module also comprises a resilient element that resists axial displacement of the support members. In this embodiment, the upper end of the lower support member extends into the space surrounded by the torque resisting cuff.

In still another embodiment, a shock module comprises upper and lower support members that are coaxially supported relative to one another and capable of relative rotation and axial translation. The shock module also comprises a generally tubular shaped torque resisting cuff that provides torsional resistance to relative rotational motion between the support members. The torque resisting cuff is proximally attached to an outer surface of one of the support members and is distally attached to an outer surface of the other support member. A resilient element resists axial displacement of the support members. In this embodiment, the lower support member comprises a base at its lower end. In addition, the base comprises at least a partially inclined attachment surface for attaching the shock module to a prosthetic foot member.

BRIEF DESCRIPTION OF THE DRAWINGS

A general architecture that implements the various features of certain embodiments of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE PREFERRED EMBODIMENTS

Figure 1:
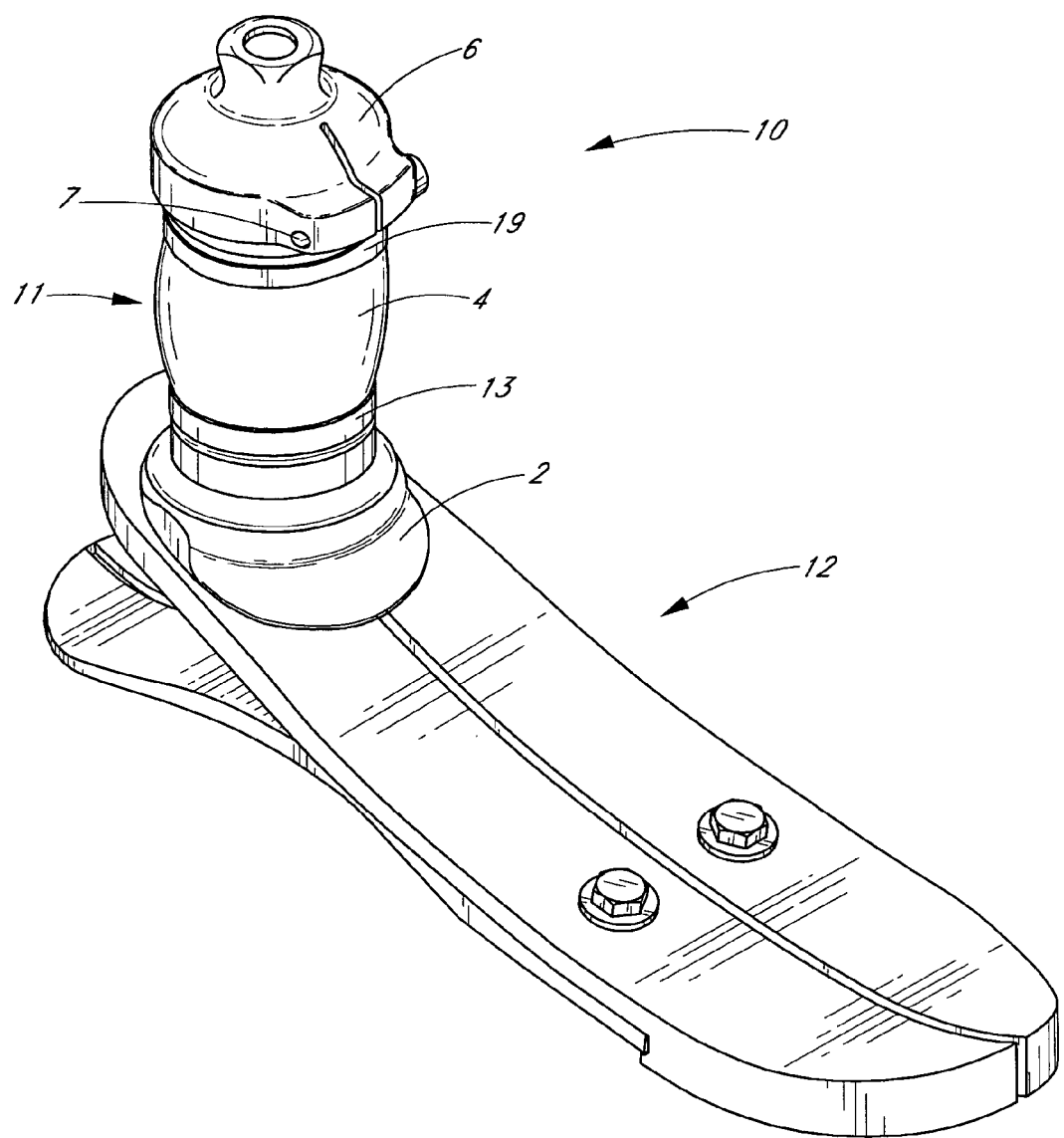
FIG. 1 is a perspective view of a lower limb prosthesis illustrating one embodiment of a shock module having features and advantages in accordance with one embodiment of the present invention.
Figure 2:
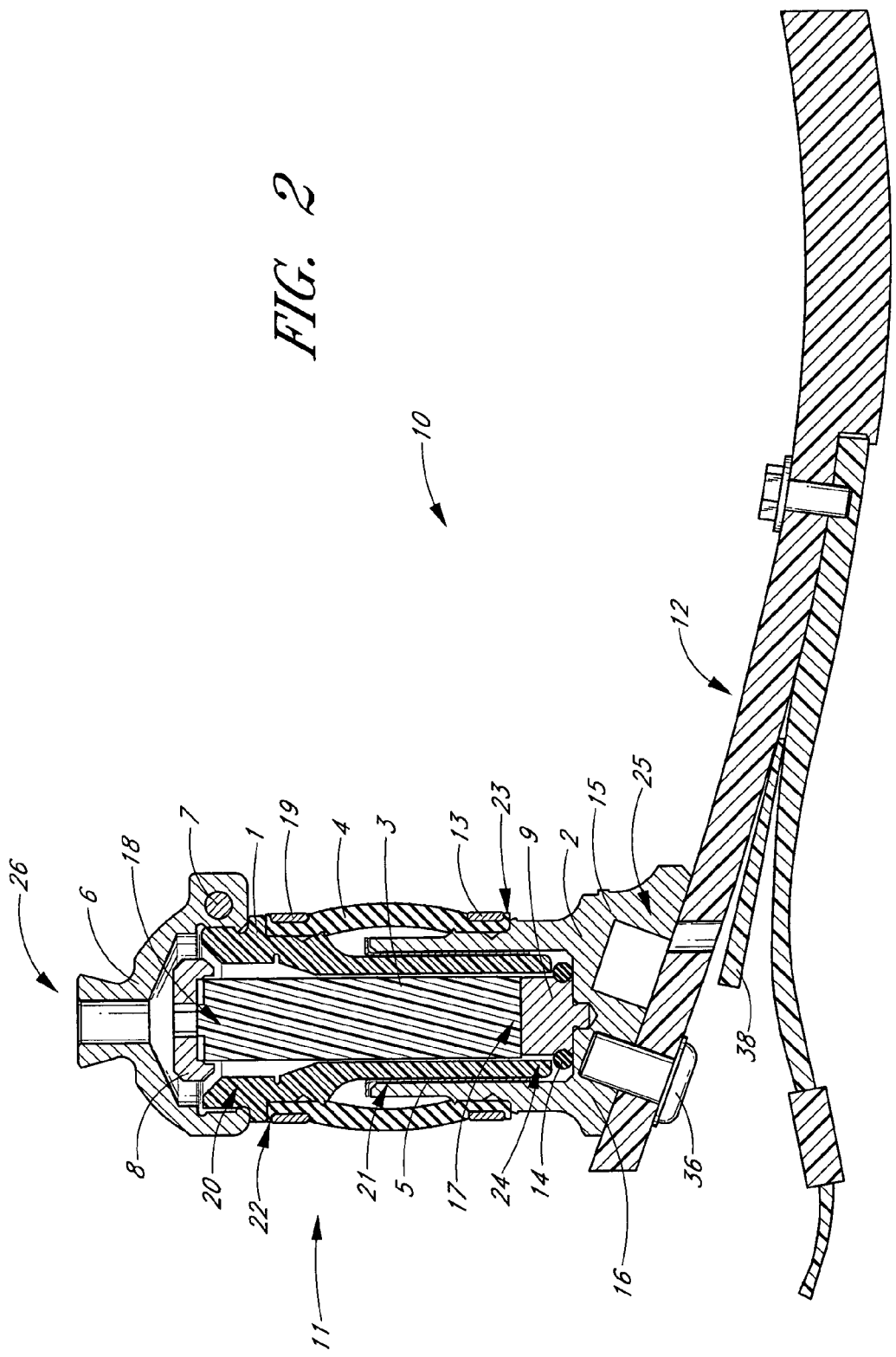
FIG. 2 is a longitudinal sectional view of a lower limb prosthesis illustrating one embodiment of a shock module having features and advantages in accordance with one embodiment of the present invention.
Figure 3B:
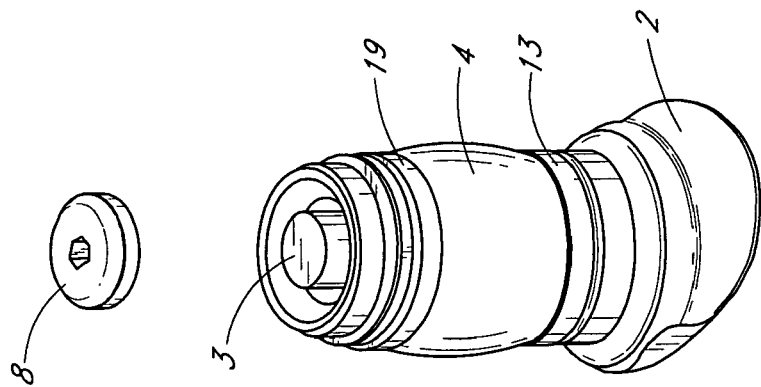
FIG. 3B is a perspective view of a preferred embodiment of the shock module of FIG. 1, illustrating a preferred embodiment of the adapter in an open position.
Figure 3A:
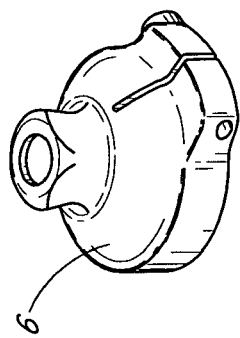
FIG. 3A is a perspective view of a preferred embodiment of the shock module of FIG. 1, illustrating a preferred embodiment of the adapter.
Figure 3A:
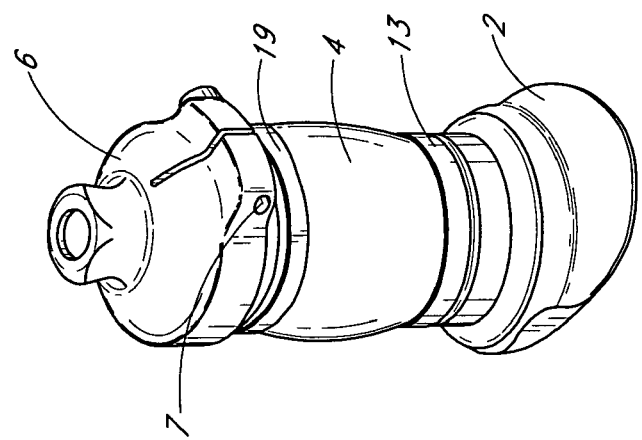
Figure 4:
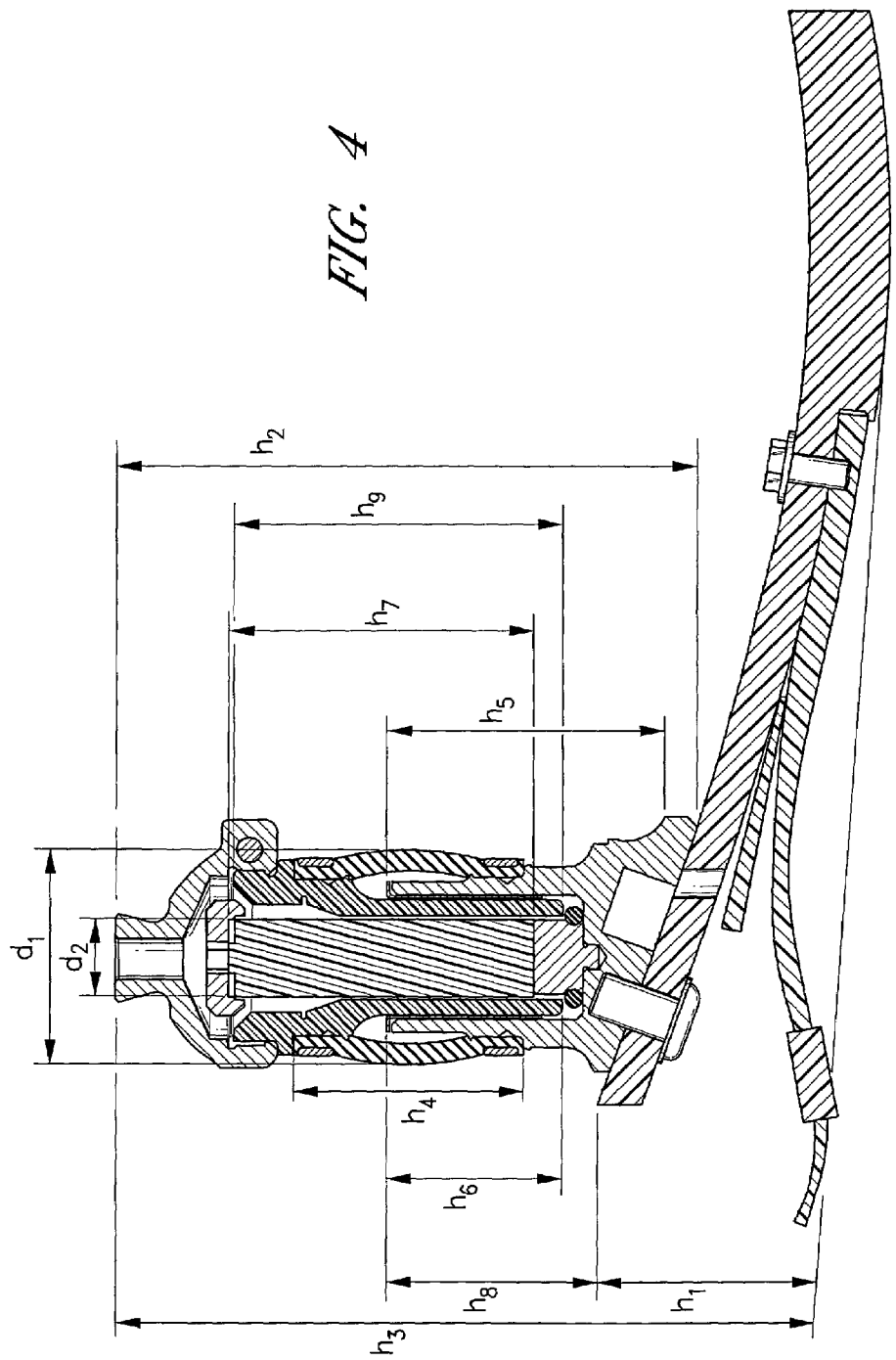
FIG. 4 is a longitudinal sectional view of a lower limb prosthesis illustrating one embodiment of a shock module having features and advantages in accordance with one embodiment of the present invention.
Figure 5:
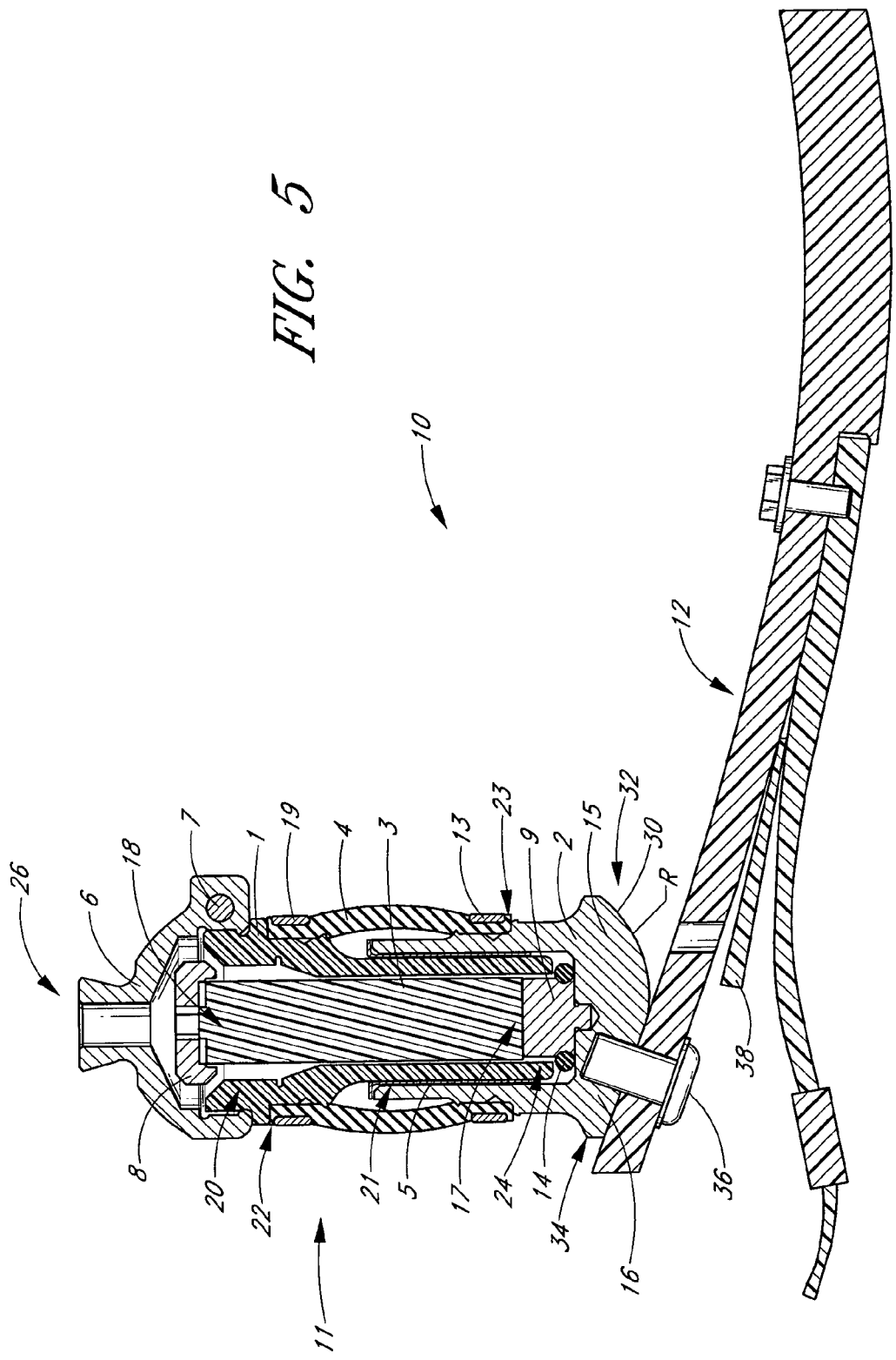
FIG. 5 is a longitudinal sectional view of a lower limb prosthesis illustrating an alternate embodiment of a shock module having features and advantages in accordance with one embodiment of the present invention.

FIGS. 1–4 show one embodiment of a lower limb prosthesis 10 comprising a shock module 11. For purposes of illustration the prosthesis 10 is shown as also comprising a prosthetic foot 12 with a wedge piece 38, in this case an LP VariFlex® foot available from Össur North America, Inc. of Aliso Viejo, Calif. It will be appreciated that the cross-section of the foot shown in FIGS. 2, 4, and 5 is purely illustrative, and does not include the slot which may bifurcate the foot in certain embodiments. The LP VariFlex® foot is described in further detail in Applicant's application entitled "Low Profile Prosthetic Foot," Ser. No. 10/642,125, filed on Aug. 15, 2003, the entirety of which is hereby incorporated by reference. It will of course be appreciated that shock module 11 can be used with any desired prosthetic foot. In certain preferred embodiments, the prosthetic foot 12 is low profile, and in one embodiment has a height $h_1$, shown in FIG. 4, not greater than about 50 mm.

As shown in FIG. 2, shock module 11 includes an inner support member 1 and an outer support member 2 each having a hollow cylindrical, tube shaped portion. The support members 1 and 2 are coaxially aligned and telescopingly engaged with one another. In the embodiment shown, inner support member 1 is an upper support member, and outer support member 2 is a lower support member, though these may be reversed. Preferably, support members 1 and 2 are slidingly and rotationally interengaged with each other while retaining their operative horizontal alignment with each other through a relatively close fit between the outside dimensions of inner support member 1 and the inside dimensions of outer support member 2. The support members 1 and 2 are preferably fabricated from a strong lightweight material, such as, for example, a carbon graphite and epoxy composite. Alternatively, one or both of the support members may be fabricated from a lightweight metal, such as age-hardened aluminum, or other metal, such as titanium. It will be appreciated that, in alternate embodiments, the support members 1 and 2 may have various different cross sectional shapes including but not limited to the following: square, rectangle, triangle, oval, or polygon.

As shown in the embodiment of FIG. 2, a flange bearing 5 can be placed between the inner support member 1 and the outer support member 2 to improve the fit and the interengagement of the support members 1 and 2. With a better fit between the support members 1 and 2 the length that the support members overlap $h_6$ can be reduced which can help reduce the overall height $h_2$ of the shock module 11. The flange portion of the bearing 5 lies along the top edge of the outer support member 2. The bearing 5 which extends downward along the inside surface of the outer support member 2, can be sized for the inner support member 1 using a sizing pin and arbor press. The bearing is preferably fabricated from a low friction material such as Teflon®.

As shown in FIG. 2, the lower end of outer support member 2 has a solid portion or base 15 that forms an attachment section for attaching the shock module 11 to a prosthetic foot 12. In one embodiment, the lower end of the outer support member 2 can be removably attached to a prosthetic foot having a horizontal attachment section using bolts, a strap or other means. Alternatively, as shown in FIG. 2, the prosthetic foot has an inclined surface 16, with bolt 36 attaching the prosthetic foot to the base 15 The base 15 preferably is also inclined to correspond to the prosthetic foot 12, and the base 15 and the surface 16 are bolted to one another. Thus, the outer or lower support 2 has two lengths, a longer length $h_5$ and a shorter length $h_8$. This arrangement allows for a lower profile, because the inclined portion of the prosthetic foot can continue to slope upward even behind the shock module 11. It will be appreciated that the shock module 11 can be attached by other means, such as those described in U.S. Pat. No. 6,478,826 and U.S. Pat. No. 6,511,512, the entirety of both of which are hereby incorporated by reference.

As shown in FIG. 2, shock module 11 includes a resilient element 3 for providing impact absorption during use of the prosthesis 10 by resisting relative axial displacement of the two support members 1 and 2. In a preferred embodiment, the resilient element 3 is a precompressed rod comprising urethane; however, other embodiments of this invention can include different types of resilient elements such as a spring or a compressible fluid or combination thereof. In the embodiment shown in FIG. 2, a base plug 9 and an adjustment plug 8 act with inner support member 1 to keep the resilient element 3 in a precompressed state. The plugs may be made of a polymeric material such as polyurethane, for example Delrin®. The solid portion or base 15 of outer support member 2 also provides a generally horizontal surface at the bottom of the hollow cylindrical interior portion of the outer support member 2. As shown in FIG. 1, base plug 9 sits on the generally horizontal surface at the bottom of the hollow interior portion of outer support member 2. An o-ring 14 is placed around base plug 9 on the surface at the bottom of the hollow interior portion of outer support member 2. The o-ring 14 keeps base plug 9 in place and maintains enough space for the inner support member 1 to slide between the inside surface of the outer support member 2 and the base plug 9. The inner support member 1 is positioned above the o-ring 14 inside of the outer support member 2. The resilient element 3 is placed inside of the inner support member 1 with its distal end 17 resting on top of the base plug 9. An adjustment plug 8 secured at the proximal end 20 of the inner support member 1 presses against the proximal end 18 of the resilient element 3 holding it in a precompressed state. Precompression of the resilient member can aid in adjusting the compression and stiffness. In certain preferred embodiments, the resilient member has a precompressed axial length $h_7$ of between about 50 and 70 mm, and in one embodiment, about 63 mm.

As shown in FIG. 2, a torque-resisting cuff 4 provides torsion resistance to the prosthesis and also keeps dirt and other debris from getting between the support members 1 and 2 and affecting their relative motion. The cuff 4 may be configured to provide some additional impact resistance. The cuff 4 is proximally attached to inner support member 1 and distally attached to outer support member 2. Preferably, the cuff 4 has a sufficient axial length $h_4$ between its proximal 22 and distal 23 ends to provide a desired amount of torsion-resistance. The axial length $h_4$ in one embodiment is between about 40 and 60 mm, and in one embodiment, about 47 mm. To accommodate the axial length of an appropriately sized cuff 4 while keeping the module 11 compact, the cuff 4 is preferably attached to the inner support member 1 at an intermediate location between its proximal 20 and distal 24 ends and is attached to the outer support member 2 at an intermediate location between its proximal 21 and distal ends 25. In one embodiment, the axial length of the torque resisting cuff $h_4$ is greater than about half the axial length of the inner support member $h_9$. Preferably, both attachments are made via ring clamps 13 and 19. In the embodiment shown, lower ring clamp 13 preferably surrounds inner and outer support members 1 and 2 around a lower portion of resilient rod 3, and upper ring clamp 19 preferably surrounds inner support member 1, but not outer support member 2, around an upper portion of resilient rod 3. As illustrated, outer support member 2 thus extends proximally into the space within cuff 4.

In the embodiment shown in FIG. 2, cuff 4 has a generally tubular dual-layered configuration. According to this configuration, an inner layer preferably comprises a resilient material such as rubber. The thickness of the inner layer affects the impact resistance and torsion-resistance of the shock module 11. A desired level of impact resistance is obtainable by providing a relatively thin inner layer. If the inner layer is too thick, it will increase the impact resistance to an undesirable level. However, this thickness might not provide sufficient torsion-resistance. Thus, an outer layer is provided to increase the torsion-resistance. The outer layer preferably comprises a knitted fabric consisting of a combination of various fibers, such as spectrafiber, kevlar, nylon, and polyester. The combination of fibers is advantageously selected to provide sufficient elasticity to accommodate the outward expansion of the inner resilient layer, and also to provide sufficient strength and resistance to torsion. Different outer layers may be offered providing different ranges of torsional stiffness.

The fiber pattern of the outer layer of the cuff 4 affects both the impact resistance and torsion-resistance of the shock module 11. If the fibers are aligned substantially parallel to the longitudinal axes of the support members 1 and 2, the cuff 4 provides relatively more impact resistance and relatively less torsion-resistance. Conversely, if the fibers are aligned substantially perpendicular to the longitudinal axes of the support members, the cuff 4 provides relatively less impact resistance and relatively more torsion-resistance. Preferably, the fibers of the knitted fabric are substantially oriented at an angle from the longitudinal axes of the support members, to achieve a suitable balance between the degrees of impact within the range of about 30 to 60 degrees, more preferably within the range of about 40 to 50 degrees, and most preferably about 45 degrees. Moreover, the fibers are preferably arranged in a criss-cross pattern.

As shown in FIG. 2, the inner support member 1 preferably has an enlarged outside diameter at its proximal end 20, approximately equal to the outside diameter of the outer support member 2. Similarly, the proximal end 21 of the outer support member 2 that extends inside of cuff 4 has a reduced outside diameter to prevent it from interfering with the cuff 4 when the module 11 is uncompressed. This allows the cuff 4 to have a nearly straight vertical position when the shock module 11 is uncompressed which can help to reduce the effective horizontal cross section of the cuff 4 at maximum compression. The cuff 4 may be positioned within a cosmetic ankle or cosmetic foot cover allowing it to be positioned closer to the ground to keep total height of the prosthesis low enough to accommodate amputees with long residual limbs. A cuff with a smaller cross section can better fit within a cosmetic ankle or a cosmetic foot cover. In certain preferred embodiments, the torque resisting cuff has a maximum uncompressed diameter $d_1$ of between about 40 and 50 mm, and in one embodiment, about 44 mm. Similarly, reducing the diameter of the resilient member $d_2$ can help to reduce the effective horizontal cross section of the shock module. In certain preferred embodiments, the resilient member has a maximum diameter $d_2$ of between about 10 and 20 mm, and in one embodiment, between about 15 and 17 mm.

FIGS. 3A and 3B illustrate one example of an attachment construction for attaching the proximal end 26 of the shock module 11 to a stump supporting socket. A variety of other suitable attachment constructions could also be used without departing from the teachings of this invention. According to a preferred attachment construction, a male pyramid fitting 6 is fixed to the proximal end 20 of inner support member 1 and is adapted to be coupled to a female pyramid fitting. This assembly allows the shock module 11 to be proximally attached to a broad selection of prosthetic sockets or other intermediate prosthetic devices, such as a prosthetic knee. Fitting 6 is preferably removably attached to the inner support member 1 with a pinch bolt 7 so that fitting 6 can be removed from the shock module 11 to allow for replacement of the resilient member 3 as shown in FIG. 2B. Alternatively, fitting 6 may be removably attached to the inner support member 1 through the use of a hinge or a threaded engagement between the exterior surface of the fitting and the interior surface of the inner support member 1. In another embodiment, fitting 6 may be adhesively bonded to the inner support member 1, using for example, 3M #420/460 toughened epoxy. Fitting 6 is preferably formed from titanium, but may be formed from other suitable materials keeping in mind the goals of strength, light-weight, and maintaining a strong bond/attachment to the inner support member 1.

During the gait cycle of normal ambulation there is axial motion between the support members 1 and 2. Upon heel strike, the inner support member 1 begins to slide down to cause the aforementioned resilient element 3 to compress and store energy. Maximum compression and storage of energy occurs as the amputee's weight shifts from the heel region of the prosthetic foot towards the toe region. Then, as the amputee's weight shifts closer to the toe region, the resilient element begins to expand and release stored energy, providing beneficial lift and thrust forces to the amputee. A prosthetist, or the amputee, can adjust the degree of impact absorption by selectively replacing the resilient element 3. In one embodiment, the maximum axial displacement between the support members is no more than about 20 mm, more preferably no more than about 15 mm, and in one embodiment, about 9–10 mm.

Shock module 11 provides smooth rotational compliance of the prosthesis. Cuff 4 is designed to resist the relative rotation of support member 1 and 2, and at the same time provide some rotational compliance therebetween. As support members 1 and 2, rotate relative to each other, the top and bottom ends of cuff 4 are likewise twisted with respect to one another. However, the cuff 4 is resistant to such twisting and provides a torsional force opposite to the direction of rotation/twisting. Moreover, as a particular twisting motion is enhanced, the oppositely directed torsional force increases. Thus, the cuff 4 operates like a torsion spring, in that it resists any incremental rotation of the support members 1 and 2, relative to each other.

In addition, shock module 11 may be short enough to accommodate the needs of amputees with long residual limbs. The shock module 11 can be offered in several different heights and sizes to accommodate a variety of different needs. The total height $h_3$ of a lower limb prosthesis including this shock module and not including a cosmetic cover in one embodiment is about 160 mm or less, more preferably within the range of about 140 mm to 160 mm. For example, one embodiment has a total height of 145 mm, another embodiment has a total height of 152 mm, and another has a total height of 157 mm.

In an alternate embodiment shown in FIG. 5, the anterior section 32 of the base 15 can comprise an edge 30 that curves upwards and away from the prosthetic foot 12. In this embodiment, the base 15 is configured to roll-up onto the foot member 12. As shown in FIG. 5, the edge 30 curves at a radius R such that the base 15 rolls-up onto the foot member 12 during motion of the foot. The radius of curvature R is preferably between about 0.5 and 4 cm. In certain preferred embodiments, the radius of curvature R is about 1 cm. However, the edge 30 need not be curved or have a radius R for the base 15 to roll-up onto the prosthetic foot 12. In another embodiment (not shown), the base 15 of the shock module 11 may be substantially flat and extend from the posterior section 34 to the anterior section 32 so as to define a longitudinal gap between the base 15 and the foot member 12. Accordingly, during motion of the foot, the anterior portion 32 can move relative to, or roll-up onto, the prosthetic foot 12. In another embodiment (not shown), the base 15 can comprise a flat portion and a curved portion. For example, the base 15 can have a generally flat portion at the posterior section 34 and a generally curved portion at the anterior section 32. In another embodiment (not shown), the base 15 can have a generally curved portion at the posterior end 34 and a generally flat portion at the anterior section 32. In still another embodiment (not shown), the base 15 can comprise multiple generally flat portions, or ledges, each inclined at a different angle relative to the support surface 16. The roll-up feature of this embodiment is described in further detail in applicant's application entitled Low Profile Prosthetic Foot, Ser. No. 10/642,125, filed on Aug. 15, 2003, the entirety of which is hereby incorporated by reference.

Further details of shock modules and prosthetic feet that include features that may be incorporated into the embodiments above are disclosed in U.S. Pat. No. 6,478,826 and U.S. Pat. No. 6,511,512, the entirety of both of which are hereby incorporated by reference.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A shock module comprising:
   an upper support member and a lower support member, said upper and lower support members being coaxially supported relative to one another and capable of relative rotation and axial translation;
   a torque resisting cuff providing torsional resistance to relative rotational motion between said support members, wherein said cuff has a generally tubular shape and is proximally attached to an outer surface of one of said support members and distally attached to an outer surface of the other of said support members; and
   a resilient element resisting axial displacement of the support members;
   wherein said lower support member comprises a base at a lower end thereof and said base comprises at least a partially inclined attachment surface for attachment to a prosthetic foot member.

2. The shock module of claim 1, further comprising a prosthetic foot member comprising an inclined attachment surface attached to said lower support member.

3. The shock module of claim 1, wherein the axial length of the torque resisting cuff is greater than about half the axial length of the inner support member.

4. The shock module of claim 1, further comprising a bearing between the inner and outer support members.

5. The shock module of claim 1, wherein the torque resisting cuff has a maximum uncompressed diameter of less than about 50 mm.

6. The shock module of claim 1, wherein the maximum axial displacement of one support member relative to the other support member is no more than about 20 mm.

7. The shock module of claim 1, wherein said shock module has a maximum axial length of no more than about 130 mm.

8. The shock module of claim 1, wherein the resilient element comprises a urethane rod.

9. The shock module of claim 1, wherein the resilient element has a diameter of no more than about 20 mm.

10. The shock module of claim 1, wherein the resilient element has a precompressed axial length of less than about 70 mm.

11. The shock module of claim 1, further comprising an o-ring place under the distal end of the inner support member.

12. The shock module of claim 1, wherein the base includes a roll up surface.

* * * * *